United States Patent [19]
White

[11] Patent Number: 5,257,636
[45] Date of Patent: Nov. 2, 1993

[54] APPARATUS FOR DETERMINING POSITION OF AN ENDOTHRACHEAL TUBE

[75] Inventor: Steven J. White, 250 Ashington Ct., Brentwood, Tenn. 37027

[73] Assignees: Steven J. White; Deborah O. White, Brentwood, Tenn.

[21] Appl. No.: 679,539

[22] Filed: Apr. 2, 1991

[51] Int. Cl.⁵ ............................................. A61B 19/00
[52] U.S. Cl. ................................... 128/897; 128/772; 128/653.1
[58] Field of Search ............ 128/653.1, 897–899, 128/772, 200.026, 207.014, 207.015

[56] References Cited

U.S. PATENT DOCUMENTS

| | | | |
|---|---|---|---|
| 3,847,157 | 11/1974 | Cailouette et al. | 128/653.1 |
| 4,173,228 | 11/1979 | Van Steenwyk et al. | 128/653.1 |
| 4,244,362 | 1/1981 | Anderson | 128/207.14 |
| 4,296,376 | 10/1981 | Bartol | 128/117 R |
| 4,431,005 | 2/1984 | McCormick | 128/207.14 |
| 4,593,687 | 6/1986 | Gray et al. | 128/200.26 |

OTHER PUBLICATIONS

Hauser et al., "Prospective Evaluation of a Nonradiographic Device . . . ", 1990.
Engler, "Verifying Endotracheal Tube Placement with the Trach Mate TM . . . ", Aug. 1989.
Andriani et al., "Complications of Endotracheal Intubation", Jun. 1988.

*Primary Examiner*—Kyle L. Howell
*Assistant Examiner*—J. P. Lacyk
*Attorney, Agent, or Firm*—Howard J. Greenwald

[57] ABSTRACT

An apparatus for determining the optimum position of an endotracheal tube while allowing simultaneous ventilation of a patient with the endotracheal tube is disclosed. This apparatus contains a stylet, connecting means for adjustably and removably disposing the stylet within an endotracheal tube, means attached to the stylet for producing magnetic flux, and means for sensing the presence of magnetic flux.

20 Claims, 4 Drawing Sheets

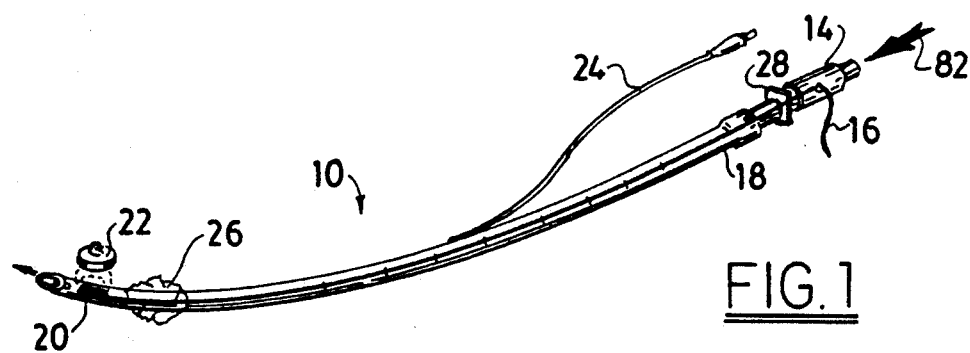
FIG. 1
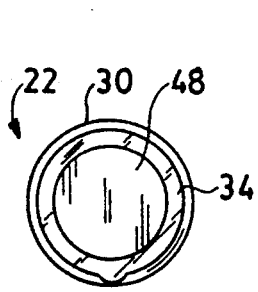
FIG. 3
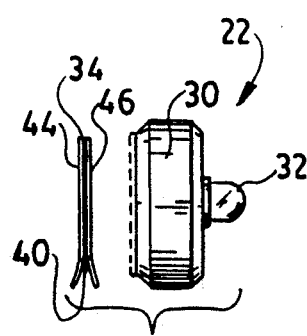
FIG. 2
FIG. 2A
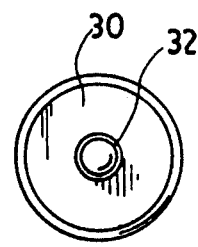
FIG. 4
FIG. 4A
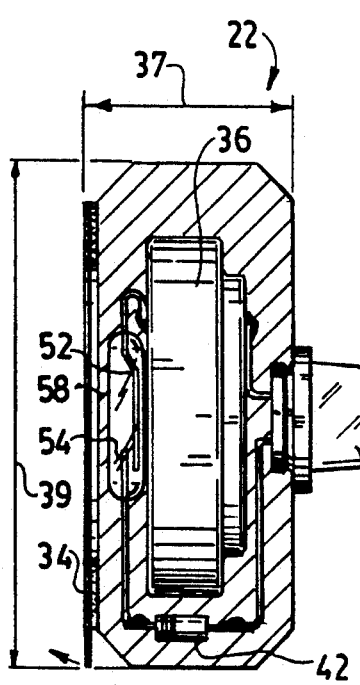
FIG. 5
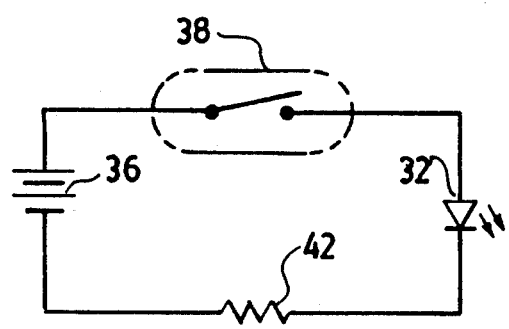
FIG. 6

APPARATUS FOR DETERMINING POSITION OF AN ENDOTHRACHEAL TUBE

FIELD OF THE INVENTION

An apparatus for determining the optimum position an endotracheal tube should be placed within a patient's trachea is disclosed.

BACKGROUND OF THE INVENTION

There are many emergency situations in which it is essential to rapidly and accurately place a endotracheal tube into a patient's trachea. Thus, for example, when a patient exhibits signs and symptoms of cardiopulmonary arrest, respiratory failure, airway obstruction, severe head injury, poisoning, and/or drug overdose, it is often critical to protect the patient's airway and/or to ventilate the patient's lungs as readily as possible. In many cases, death or severe injury often results from a failure to accurately and rapidly perform this procedure.

The endotracheal tube must be precisely positioned within the patient's airway; it should be neither too high nor too low in the trachea.

If the tube is not inserted far enough into the trachea, it can cause severe damage. In the first place, it might not protect against aspiration of the patient's stomach contents; such aspiration can choke the patient and cause his death. In the second place, it is more likely to be readily dislodged whe placed too high. In the third place, air delivered through the tube may flow, in part or whole, through the patient's mouth and/or nose and not adequately ventilate his lungs. In the fourth place, the misplaced tube might severely damage the patient's vocal cords.

If the endotracheal tube is inserted too far into the patient's trachea, it often causes other severe problems. As is indicated by a article by J. Adriani et al. entitled "Complications of Endotracheal Intubation" (Southern Medical Journal, Volume 81, No. 6, pages 739-744), the trachea bifurcates at the level of the second rib. If the endotracheal tube is inserted beyond this bifurcation point, only one lung will be ventilated by the tube, thereby often causing the other lung to collapse; and a failure to provide oxygen to both lungs may cause a potentially fatal oxygen deficit to occur. Furthermore, delivery of all of the volume of air to the one lung may damage that lung.

One means of insuring that the endotracheal tube has been properly inserted into a patient's trachea is to conduct a x-ray of the patent's chest. However, this is a rather time-consuming, expensive procedure which, in the case of malpositioning of the endotracheal tube, must be repeated until analysis indicates proper placement. The luxury of conducting repeated chest x-rays is often not available in life-and-death situations in which it is essential to properly and speedily place the endotracheal tube. Ambulances, for example, do not contain portable x-ray machines.

The prior art has attempted to provide inexpensive, accurate means of placing a endotracheal tube within a patient's trachea; such attempts have only met with limited success.

In an article by Gabriel Hauser et al., entitled "Prospective evaluation of a nonradiographic device for determination of endotracheal tube position in children," Critical Care Medicine, Volume 18, No. 7 (1990), at pages 760-763, a discussion of the "TRACH-MATE" intubation system is presented; this system is sold by McCormick Laboratories of North Chelmsford, Mass. As is indicated in this article (at page 760), this device ". . . consists of a sterile, single-use, polyvinyl chloride ETT [endotracheal tube] which contains a magnetically detectable metallic element within the tube wall at a defined distance from the distal tip of the tube . . . . A portable, battery-powered locator instrument has a 1.3-cm diameter pointer probe, and is capable of detecting the marker transcutaneously. The instrument operates by detecting the change of the alternating magnetic field emitted by the probe when the field is perturbed by the presence of the metallic interference element embedded in the ETT wall."

The prior art has recognized certain limitations in the use of the "TRACH-MATE" system. Thus, in an article by Arthur Engler entitled "Verifying Endotracheal Tube Placement With the TRACH MATE . . . Intubation System," appearing in Pediatric Nursing, July-August, 1989, Volume 15, No. 4 (at pages 390-392), it is disclosed that: "Use of the TRACH MATE . . . endotracheal tube is contraindicated in cases in which the infant has metallic or magnetic objects or devices located near the trachea . . . . Special care should be used when magnetic resonance imaging . . . scans are needed on patients with the TRACH-MATE endotracheal tube in place. Image distortion of anatomical locations near the tube's magnetic marker in the trachea may occur." (at page 391)

Even when the "TRACH-MATE" system is used in situations where it is indicated, the results obtained have been disappointing. As reported in the aforementioned article appearing in Critical Care Medicine, Hauser and his colleagues conducted several studies with the "TRACH-MATE" system. In one study of twenty children, summarized in Table 2 (at page 762), ten of the twenty placements of the endotracheal tube with the "TRACH-MATE" system were incorrect: eight were too high, and two were too low.

In addition to the high-failure rate reported by Hauser et al. for the "TRACH-MATE" system, other problems are presented by this system. In the first place, it requires the use of a special endotracheal tube which contains metallic material embedded on its inside surface; this special tube is not widely available or widely used, and it is not believed to be available in sizes suitable for use in adults. In the second place, it is rather expensive, costing in excess of five-hundred dollars for the locator instrument used in the system. In the third place, it requires at least two operators to properly use during intubation; one of the operators must hold the laryngoscope (which is used to visualize the vocal cords) while inserting the endotracheal tube, while another operator must hold the locator in place on the patient's chest. In the fourth place, the device should not be used when any metallic objects are near the patient's trachea. In the fifth place, the special endotracheal tube required (which costs in excess of $7.00) is not reusable.

It is a object of this invention to provide an apparatus for rapidly and properly positioning an endotracheal tube within a patient's trachea whose use will result in a substantially higher percentage of proper positionings than the prior art systems.

It is another object of this invention to provide an apparatus for properly positioning an endotracheal tube within a patient's trachea which is both reusable and relatively inexpensive.

It is another object of this invention to provide an apparatus for properly positioning an endotracheal tube within a patient's trachea which can be used with conventional, inexpensive, readily available endotracheal tubes.

It is another object of this invention to provide an apparatus for properly positioning an endotracheal tube within a patient's trachea which, while the endotracheal tube is being positioned, allows the patient to be ventilated.

It is yet another object of this invention to provide an apparatus for checking the placement of endotracheal tubes which have bee positioned in a patient by other means.

SUMMARY OF THE INVENTION

In accordance with this invention, there is provided an apparatus for determining the optimum position of an endotracheal tube. This apparatus contains a stylet, connecting means for adjustably and removably disposing the stylet within an endotracheal tube, means attached to the stylet for producing magnetic flux, and means for sensing the presence of magnetic flux.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 1 is a perspective view of a preferred apparatus of this invention;

FIG. 2 is a side view of one preferred magnetic flux sensing device which is used in the apparatus of FIG. 1;

FIG. 2A is a side view of another preferred magnetic flux sensing device;

FIG. 3 is a bottom view of the sensing device of FIG. 2;

FIG. 4 is an end view of the sensing device of FIG. 2;

FIG. 4A is an end view of the sensing device of FIG. 4;

FIG. 5 is a sectional view of the sensing device of FIG. 2;

FIG. 6 illustrates one electrical means of activating the sensing device of FIG. 2;

DESCRIPTION OF THE PREFERRED EMBODIMENTS

Figure 7:
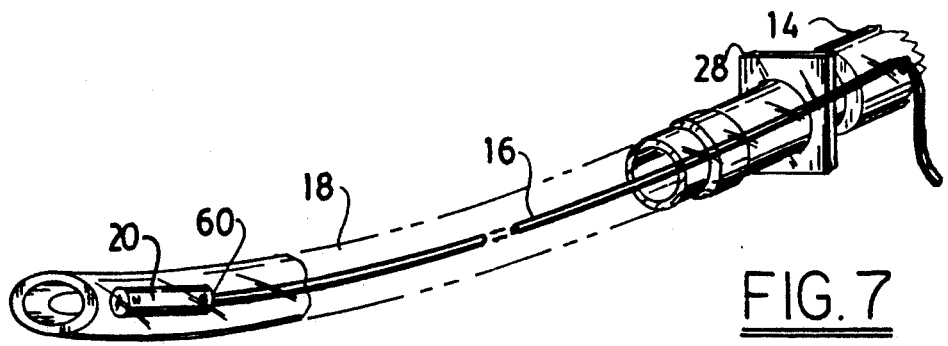
FIG. 7 is a partial sectional view of the apparatus of FIG. 1, showing the stylet disposed within an endotracheal tube and connected to a means for producing magnetic flux.

FIG. 1 is a perspective view of one preferred embodiment of the invention. Referring to FIG. 1, it will be seen that air from a ventilating source (not shown) is introduced into apparatus 10 in the direction of arrow 12. It will be seen that apparatus 10 is preferably comprised of a adaptor 14, a stylet 16 which is adjustably and removably attached to adaptor 14, an endotracheal tube 18, a means for producing magnetic flux 20, a means for sensing magnetic flux 22, and a pilot balloon 24 which may be used to inflate cuff 26.

As is know to those skilled in the art, most standard endotracheal tubes come equipped with a proximal adaptor 28 which has an outside diameter of 15 millimeters and with pilot balloon 24 and cuff 26. These endotracheal tubes are readily available and may be purchased from Baxter, Incorporated through the Baxter Hospital Supply Division, 1955 Wehrle Drive, Williamsville, N.Y. 14221. Reference also may be had to U.S. Pat. Nos. 4,244,362 and 4,063,561 which also illustrate the construction of an endotracheal tube; the disclosure of each of these patents is hereby incorporated by reference into this specification. Thus, referring to FIG. 1 of U.S. Pat. No. 4,244,362, proximal adaptor 21, pilot balloon 19, and cuff 17 are illustrated.

One preferred magnetic sensing means is illustrated in FIG. 2. Referring to FIG. 2, magnetic sensing means 22 is preferably comprised of a body 30, an indicator 32, and a means 34 for removably attaching sensing means 22 to a patient's neck.

Means for sensing the presence of magnetic flux are well know to those skilled in the art. Thus, by way of illustration, U.S. Pat. No. 4,296,376 of Bartol describes a probe for sensing energizations of electrical components; the disclosure of this patent is hereby incorporated by reference into this specification. The probe of the Bartol patent is comprised of (1)a non-magnetic housing, (2)a magnetizable switch forming a pair of contactable members mounted within said housing, wherein at least one of said members is movable in the housing relative to the other for engaging the other when in a magnetic field, (3)a lamp, (4)battery means having a pair of terminals, and (5)a first means for connecting the lamp and the members in a series arrangement across the terminal of the battery means. When said members are exposed to a first magnetic field, a lamp is activated.

The circuit used in the device of the Bartol patent is illustrated in FIG. 1 of such patent (and in FIG. 6 of this application) and is comprised of a source of direct current, a switch, a light-emitting diode, and a resistor. The switch used in this circuit is often referred to as a "magnetic reed switch." This switch is described in column 4 of the Bartol patent. Referring to column 2 of such patent, it will be seen that switch 12 comprises two magnetic reeds 15 and 16 mounted inside a non-magnetic housing 17 with lead wires 18 and 19 connected, respectively, , to reeds 15 and 16 and brought out as electrical terminals through one end of housing 17. At least one of the reeds 15 and 16 is pivotally mounted or is sufficiently flexible so that, whe relay 12 is placed in a magnetic field, a portion of the field is intercepted by the reeds 15 and 16 with the consequence that reeds 15 and 16 are draw together by their resulting magnetization and electrical contact between reeds 15 and 16 is thereby effected. Relays of this type are produced by Sigma Instrument (Part 3A31-103).

As is well know to those skilled in the art, dry and mercury wetted magnetic reed switches which are hermetically sealed are also available from other vendors. Thus, for example, such switches are discussed on page 386 of the Newark catalog 110 (Newark Electronics, Chicago, Ill., 1989). The use of these reed switches is preferred, for they are not affected by any atmospheric conditions, temperatures, or pressure.

The probe described in the Bartol patent is commercially available, and it may be obtained from Bartol Research of 931 East 10th Place, Mesa, Ariz. (as "Magprobe").

Although the magnetic flux sensing device of the Bartol patent, and the magnetic flux sensing device of this patent application, use a lamp as an indicator, it will be apparent to those skilled in the art that a sound generating device (such as a buzzer) could also be used. Magnetic flux sensing circuits comprised of a sound-generating indicator are well know to those skilled in the art and are described in, e.g., Rudolf F. Graf's "The Encyclopedia of Electronic Circuits" (Tab Books Inc., Blue Ridge Summit, Pa., 1985). Alternatively, or additionally, other indicators may be used. Alternatively, more than one indicator may be used in a given sensing device 22.

Referring to FIG. 6, a typical circuit which may be used in applicant's claimed device is shown. This circuit is comprised of a source of direct current 36, a reed switch 38, a lamp 32, and an optional, current-limiting resistor 42. The circuit described in FIG. 6 is similar to and operates like the circuit described in FIG. 1 of the Bartol patent.

The lamp 32 is preferably a light-emitting-diode ("LED") which consumes a relatively low amount of power. This type of LED device is extensively discussed at columns 4 and 5 of the Bartol patent, and it is well know to those in the art.

Referring again to FIG. 2, it will be seen that magnetic sensing means 22 is comprised of a means 34 for removably attaching sensing means 22 to a patient's body. Any conventional means for so removably attaching the sensing means to a patient's body may be used. By way of illustration, one may use O-rings with adhesive on each of their sides. Such an O-ring 34 is illustrated in FIG. 2; it is comprised of an annular, elastomeric section 40 with an orifice in its center, and adhesive sections 44 and 46, each of which are also annular and have an orifice through their centers. FIG. 3 illustrates the O-ring 34 attached to the body 30 of the sensing means 22, and it illustrates the orifice 48 which extends through the O-ring.

FIG. 2A illustrates one embodiment of magnetic sensing means 22 in which such sensing means is provided with a shield 50 to prevent ambient light from interfering with the light output of the device. In the embodiment illustrated in FIG. 2A, shield 50 is preferably integrally formed with body 30. In another embodiment, not shown, shield 50 is removably attached to body 30.

FIG. 5 illustrates one preferred sensing device 22, which is comprised of reeds 52 and 54, and which preferably is encapsulated by plastic container 58. The structure of this reed switch circuit is similar to the structure of the reed switch circuit illustrated in the Bartol patent.

In one embodiment, not shown, the means 22 is comprised of at least two indicators 32 and at least two reed switches 38. The use of two or more combinations of reed switches 38 and indicators 32 allows the device 22 to indicate at what portion of the device the magnetic flux is strongest. Thus, by way of illustration, if one such reed switch/indicator combination is located in the front of device 22 and another such combination is located in its rear, whe the magnetic flux is strongest in the area near the front part of the device the indicator located therein will produce an appropriate signal. By the use of a multiplicity of reed switch/indicator combinations, the precise point of maximum magnetic flux can be indicated. Such a combination also will enable one to determine the point of minimum magnetic flux.

In the preferred embodiment illustrated in FIG. 5, the preferred means 22 for sensing the presence of magnetic flux has a height 37 which is preferably from about 1 to 2 centimeters and, more preferably, from about 1 to about 1.5 centimeters; this height does not include the height of indicator 32, which may be from about 0.5 to about 1.0 centimeter in height.

Means 22 preferably has a width 39 which is from about 1.5 to about 2.5 centimeters.

In one embodiment, means 22 has a substantially circular cross-section, with a diameter 39 of from about 1.5 to about 2.5 centimeters.

FIG. 7 is a view of the stylet 16 of this invention disposed within endotracheal tube 18.

The proximal end 60 of stylet 16 of this invention is attached to a means 20 for producing magnetic flux.

Any magnetic flux producing means with the desired magnetic field strength may be used as means 20. In the embodiment illustrated in FIG. 7, a permanent magnet is used to produce the magnetic flux.

The means 20 must produce a specified field strength; it should be sufficiently strong that, at a distance of 3.0 centimeters from sensor 22, it will activate the sensor. Thus, in one preferred embodiment, where the reed switch 38 is activated by a 5 Gauss of flux, when magnet 20 is measured at a distance of 3.0 centimeters with a conventional Gaussmeter, the magnet will exhibit a magnetic induction of at least about 5.0 Gauss.

Suitable magnetic materials which may be used in magnet 20 are well know to those skilled in the art and are described, e.g., in "Testing and Measurement of Permanent Magnets" (Magnetic Materials Producers Association, 1717 Howard Street, Evanston, Ill., 1975); page 8 of this publication lists the composition of typical magnetic materials.

In one preferred embodiment, magnet 20 is a rare earth magnet. As is know to those skilled in the art, a rare earth magnet is comprised of one or more rare earth metals such as, e.g., Samarium, Praseodymium, Cerium, Yttrium, Neodymium, and the like. Thus, by way of illustration, the magnet may be an alloy of Neodymium, Iron, and Boron which is commercially available as "Rare Earth Magnets," Catalog Number 64-1895, Radio Shack, Fort Worth, Tex.

Referring to FIG. 8, it will be seen that magnet 20 preferably has a length 21 of from about 0.5 to about 3.0 centimeters.

Figure 8A:
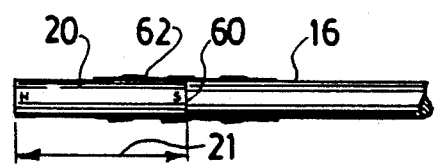
FIGS. 8A, 8B, 8C, and 8D each illustrate an alternative means for attaching a magnet to the end of the stylet used in applicant's apparatus.
Figure 8B:
Figure 8C:
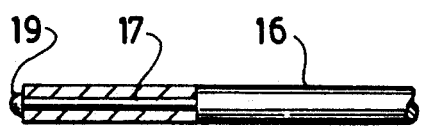
Figure 8D:

Referring to FIGS. 8A, 8B, 8C, and 8D, it will be seen that magnet 20 may be secured to the end 60 of stylet 16 by conventional means. Thus, as is show in FIG. 8A, the magnet 20 may be secured to stylet 16 by shrink-wrap tubing 62. As indicated in FIG. 8B, these components may be attached to each other by encapsulation within a suitable resin 64. Alternatively, as shown in FIG. 8C, a portion 17 of stylet 16 may be turned dow to a smaller diameter and inserted through an orifice in the magnet; at the point at which portion 17 exits the magnet, it may be formed into a head 19. FIG. 8D illustrates joining the components by threading a portion of the interior of magnet 20, turning down a portion 17 of stylet 16, forming male threads on the smaller portion 17 of the stylet, and screwing the stylet into the magnet. In another embodiment, not shown, stylet 16 and magnet 20 are joined by suitable adhesive means. Other joining means will be apparent to those skilled in the art.

In one embodiment, a stylet with a magnet attached to its end is produced in accordance with the teaching of U.S. Pat. No. 4,244,362 of Anderson, the disclosure of which is hereby incorporated by reference into this specification.

Substantially any of the prior art stylets may be joined to a source of magnetic flux 20 to produce the stylet 16 of this invention. As is know to those skilled in the art, a stylet is a device which fits inside an endotracheal tube and assists in directing the insertion of the tube by making the tube more rigid and allowing its shape to be changed. See, for example, Jerry A. Dorsch et al.'s "Understanding Anesthesia Equipment" (The Wilkins and Wilkins Company), pages 274–275.

The stylet 16 used in applicant's invention has a length of from about 25 to about 40 centimeters and a diameter of from about 0.125 to about 0.188 inches. In one preferred embodiment, stylet 16 consists of braided steel wire. One suitable braided steel wire which may be used Archer's "Plastiguard Guy Wire," which is available as Catalog Number 15-037 from Radio Shack, Fort Worth, Tex.

One essential part of applicant's invention is adaptor 14, which allows one to simultaneously ventilate a patient as the endotracheal tube is being positioned within the trachea. Inasmuch as such positioning may take time, the ability to ventilate while it occurs often is important.

Figure 9:
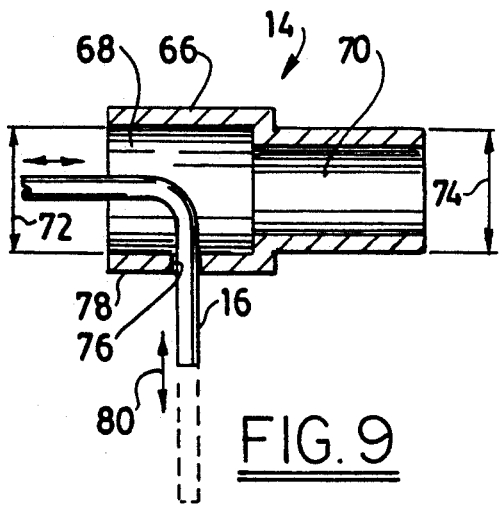
FIGS. 9 and 10 illustrate one means of attaching a stylet to a preferred adaptor used in the apparatus of FIG. 1.
Figure 10:
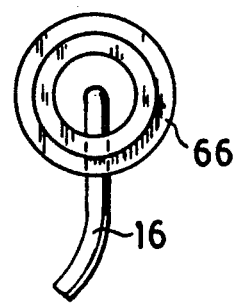

Referring to FIG. 9, it will be seen that adaptor 14 is comprised of a body defining two stepped, concentric bores 68, and 70. The diameter of one of the bores is always about 15 millimeters; thus, e.g., referring to FIG. 9, bore 68 may have a diameter 72 of about 15 millimeters. The diameter of the other section (such as stepped bore 70) may be either greater or smaller than the diameter of the first section. In one embodiment, not shown, stepped bore 70 has an inner diameter of about 22 millimeters. In the embodiment shown in FIG. 9, stepped bore 70 has an outer diameter 74 of about 15 millimeters. It will be appreciated by those skilled in the art that one end of adaptor 14 will be connected to proximal adaptor 28 of endotracheal tube 18, whereas the other end of adaptor 14 will be connected to a source of ventilation.

Adaptor 14 is comprised of a first orifice (stepped bores 68 and 70) with a minimum diameter of at least about 15 millimeters; it is also comprised of a second orifice to allow for the insertion of the stylet 16 through the body 66 of adaptor 14.

Referring to FIG. 9, it will be seen that orifice 76 preferably extends through side 78 of body 66 of adaptor 14. This orifice is substantially the same width as the outside diameter of stylet 16. It will be readily apparent to those skilled in the art that stylet 16 can be inserted through orifice 76 in the direction of arrow 80 and pushed down the endotracheal tube (not shown in FIG. 9) to its desired length; the optimum desired length will be a function of the length of the endotracheal tube, it being recommended that the stylet assembly extend to a point about 1 centimeter from the tip of the endotracheal tube (see FIG. 7). Once the optimum length has been obtained, the stylet is bent at a substantially 90 degree angle to fix the length.

Adaptor 14 preferably is an integral body which consists essentially of an inert plastic material. Any of the inert plastic materials know to those skilled in the art may be used. In one embodiment, adaptor 14 consists essentially of polycarbonate. As is know to those skilled in the art, most of the polycarbonate materials are based on a reaction between bisphenol A and carbonyl chloride. See, e.g., the "Modern Plastics Encyclopedia," Mid-October 1990 issue, Volume 67, Number 11, Modern Plastics.

Figure 11:
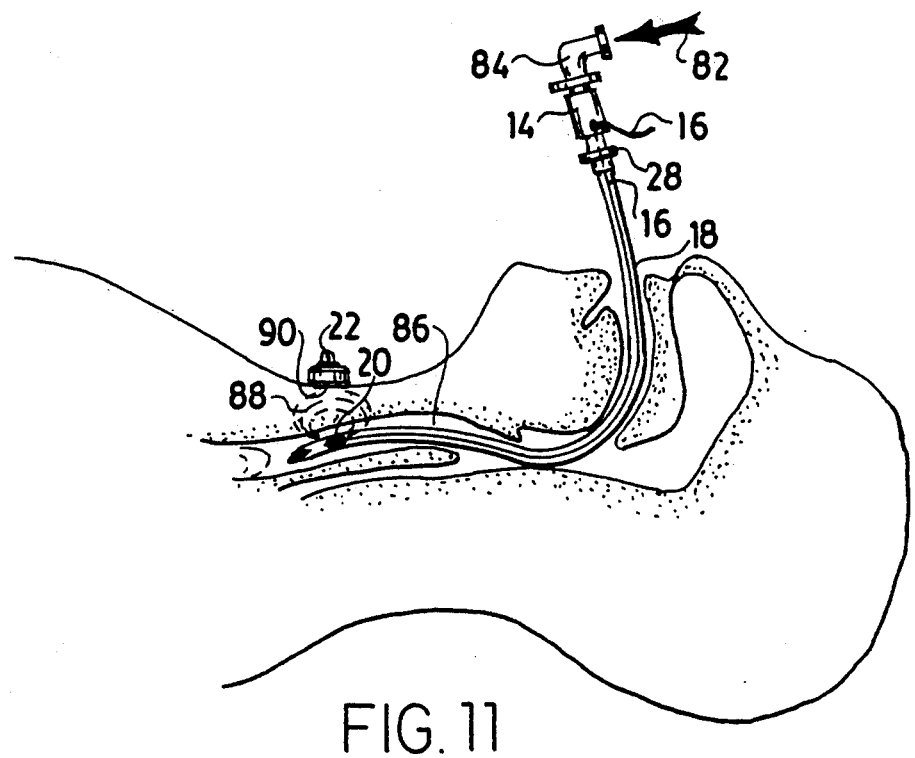
FIG. 11 illustrates the use of the apparatus of FIG. 1 in a patient's trachea.

FIG. 11 illustrates the positioning of an endotracheal tube within a patient's trachea using applicant's claimed apparatus. Referring to FIG. 11, it will be seen that, as air is introduced in the direction of arrow 82 through ventilation adaptor 84 and adaptor 14, the endotracheal tube 18 is being positioned within the trachea 86. During this process, magnetic lines of force 88 are being produced by magnet 20 and sensed by sensor 22.

Sensor 22 preferably is removably attached to the suprasternal notch 90 of the patient. The suprasternal notch, as is know to those skilled in the art, is the depression above the sternum; it is an external landmark that corresponds to the middle of the trachea. See, e.g., an article by R. D. Stewart et al., "Correct positioning of an endotracheal tube using a flexible lighted stylet," Critical Care Medicine, 18(1): 97–9, January, 1990.

Figures 12, 13:
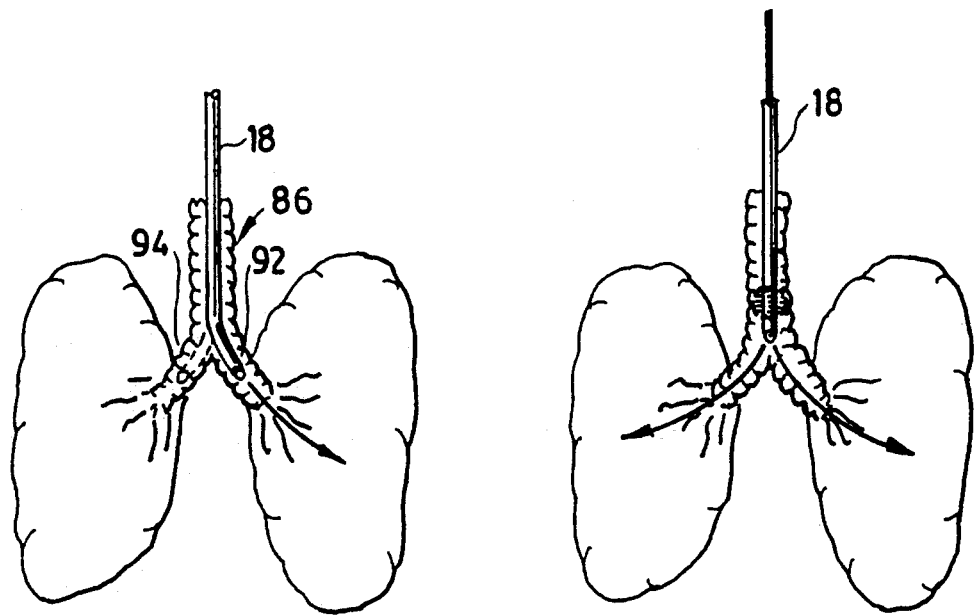
FIG. 12 shows an endotracheal tube inserted substantially past the optimum point within a patient's trachea so that such tube only ventilates one lung.
FIG. 13 shows an endotracheal tube inserted at substantially the ideal position within a patient's trachea.

Referring to FIG. 12, it will be seen that the trachea 86 bifurcates into a left bronchus 92 and a right bronchus 94. If the endotracheal tube 18 is inserted too far into the trachea, it will enter one of the bronchi (usually right bronchus 94) and, thus, the air flowing through the tube will not ventilate the other bronchus. Applicant's invention allows one to position the endotracheal tube at its optimum point (see FIG. 13) in which it ventilates both of the lungs and is securely positioned within the trachea.

FIGS. 14 through 18 illustrate the use of applicant's claimed apparatus. In each of these Figures, means for sensing magnetic flux 22 is removably attached at the suprasternal notch 90 of the patient.

Figure 14:
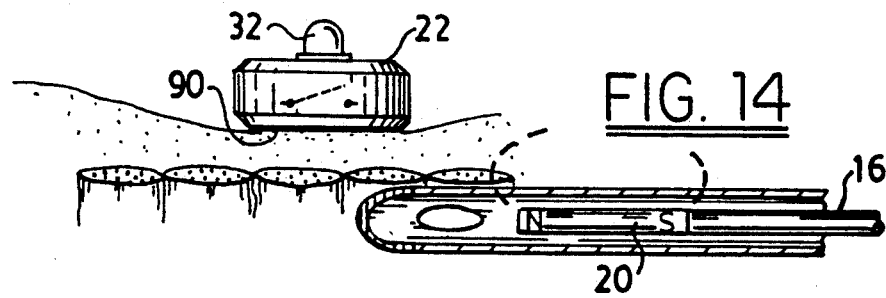
FIG. 14 through 18 illustrate how the placement of the preferred apparatus of FIG. 1 within a patient's trachea at various positions affects the output of a magnetic flux sensing device located at the base of the patient's neck.

In the situation depicted in FIG. 14, the endotracheal tube 18 is being advanced towards the midpoint of the trachea, but the magnetic flux produced by magnet 20 are not yet close enough to sensor 22 to cause indicator 32 to light. In general, lamp 32 will not light unless the magnet 20 is within from about 2 to about 4 centimeters.

Figure 15:
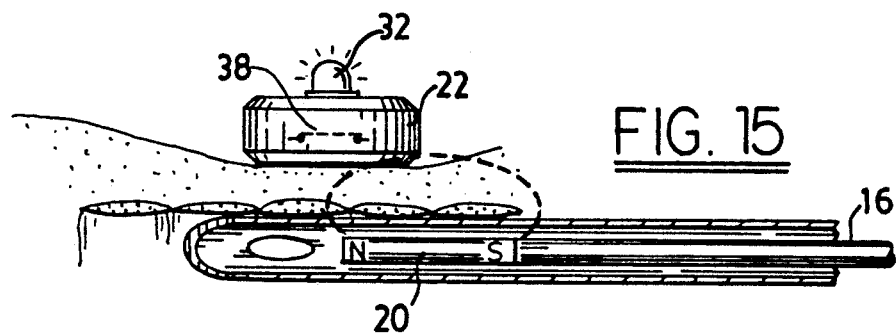

In FIG. 15, the magnet 20 been moved within from about 2 to about 4 centimeters of sensor 22, thus activating reed switch 38 and lamp 32.

Figure 16:
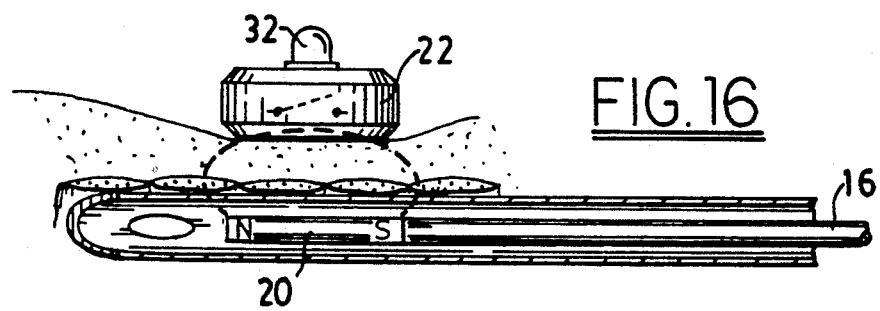

FIG. 16 illustrates what occurs when endotracheal tube is inserted further within the trachea. When the midpoint of magnet 20 is located substantially under the midpoint of sensor 22, sensor 22 experiences a substantially net zero magnetic field; the flux emanating from the north pole of magnet 20 are substantially equal to the flux emanating from the south pole of magnet 20, and thus in the position of FIG. 16 reed switch 38 is not activated.

Figure 17:
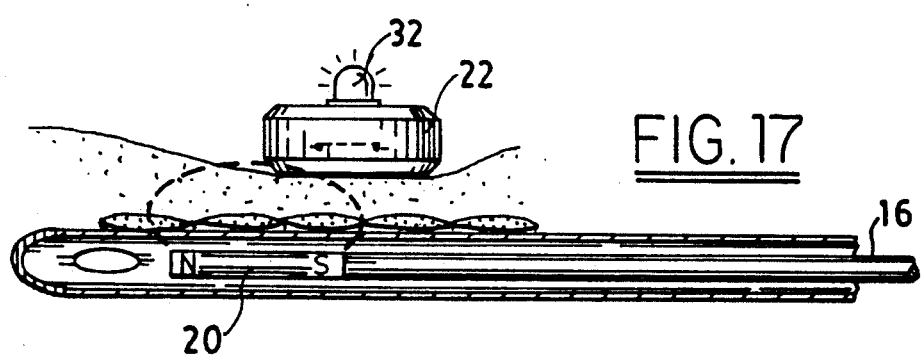

FIGS. 17 illustrates what occurs when the endotracheal tube is inserted still further into the trachea.

At the point shown in FIG. 17, magnet 20 is still within the 2-4 centimeter activation distance, and reed switch 38 and lamp 32 are activated.

Figure 18:
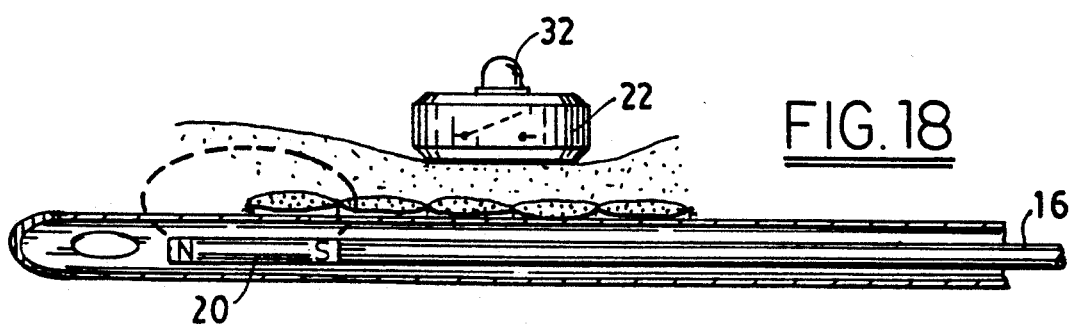

When the endotracheal tube 18 is pushed still further into the trachea, as illustrated in FIG. 18, the magnet is moved outside of the 2-4 centimeter activation distance, and the lamp 32 is not activated.

Thus, with applicant's device, one may determine both the outer limits of placement of the endotracheal tube (c.f. the positions of FIGS. 15 and 17) as well as the optimum positioning of such tube (c.f. the position of FIG. 16). The magnet 20 is so disposed within the endotracheal tube 18 (normally within about 0.5 to about 2.0 centimeters of the tip of such tube) that it will preferably activate the indicator 32 when the tube is at the locations specified in the Figures.

In one embodiment, not shown, applicant's claimed device is modified to utilize several means for sensing magnetic flux's 22. This array of sensors 22 may be arranged over the thyroid cartilage of the patient; and they will assist in determining blind intubation position.

In another embodiment, applicant's claimed device may be utilized to exclude placment of the endotracheal tube within the patient's esophagus.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. An apparatus for determining the optimum position of an endotracheal tube containing an inlet and an outlet while allowing simultaneous ventilation of a patient with said endotracheal tube, said apparatus comprising a stylet with a proximal end and a distal end, a means for producing magnetic flux connected to said distal end of said stylet, an adaptor comprised of a annular body comprising a first orifice, a second orifice, and a third orifice, means for connecting said third orifice of said adaptor with said inlet of said endotracheal tube, means for adjustably and removably connecting said stylet to said adaptor by passing said stylet through said second orifice and said third orifice until said distal end of said stylet is a specified distance from said outlet of said endotracheal tube, means for sensing the presence of said magnetic flux which is located within from about 2 to about 4 centimeters from said sensing means, and means for indicating the presence of said magnetic flux which is located within from about 2 to about 4 centimeters from said sensing means, wherein:
   (a) said first orifice has an outer diameter of about 15 millimeters, and said third orifice has an inner diameter of about 15 millimeters;
   (b) said second orifice is from about 3.75 to about 4.78 millimeters in width; and
   (c) said stylet is a coated, malleable device comprising a core consisting essentially of inorganic material and a coating of non-magnetic material.

2. The apparatus as recited in claim 1, wherein said apparatus is comprised of means for removably attaching said means for sensing the presence of magnetic flux to a patient's neck.

3. The apparatus as recited in claim 2, wherein said means for sensing the presence of magnetic flux is comprised of a magnetic reed switch.

4. The apparatus as recited in claim 3, wherein said means for indicating the presence of magnetic flux is comprised of a light-emitting diode.

5. The apparatus as recited in claim 1, wherein said apparatus is comprised of at least two means for indicating the presence of said magnetic flux.

6. The apparatus as recited in claim 5, wherein said apparatus is comprised of at least two means for sensing the presence of said magnetic flux.

7. The apparatus as recited in claim 1, wherein said means for indicating the presence of said magnetic flux is comprised of a means for producing sound.

8. The apparatus as recited in claim 2, wherein said means for removably attaching said means for sensing the presence of magnetic flux to a patient's neck is comprised of an O-ring connected to said means for sensing the presence of magnetic flux.

9. The apparatus as recited in claim 8, wherein said O-ring is comprised of adhesive means for removably attaching said O-ring to a patient's neck.

10. The apparatus as recited in claim 4, wherein said means for indicating the presence of said magnetic flux is comprised of a shield disposed around said light-emitting diode.

11. The apparatus as recited in claim 1, wherein said means for producing magnetic flux is comprised of a permanent magnet.

12. The apparatus as recited in claim 11, wherein said permanent magnet is a rare earth magnet.

13. The apparatus as recited in claim 11, wherein the both said magnet and said stylet have a substantially circular cross-section.

14. The apparatus as recited in claim 13, wherein the diameter of said stylet and the diameter of said magnet are substantially identical.

15. The apparatus as recited in claim 14, wherein said stylet has a diameter of from about 0.125 to about 0.188 inches.

16. The apparatus as recited in claim 15, wherein said stylet is comprised of braided steel wire which wire is coated with a non-magnetic substance.

17. The apparatus as recited in claim 1, wherein said stylet is comprised of indicators located on its proximal end, wherein said indicators show the length the stylet is extending through said endotracheal tube.

18. The apparatus as recited in claim 1, wherein said means for sensing the presence of said magnetic flux has a height of from about 1 to about 2 centimeters.

19. The apparatus as recited in claim 18, wherein said means for sensing the presence of said magnetic flux has a substantially circular cross-section.

20. The apparatus as recited in claim 19, wherein said means for sensing the presence of said magnetic flux has a cross-sectional diameter of from about 1.5 to about 2.5 centimeters.

* * * * *